US012678571B2

(12) United States Patent
Casey et al.

(10) Patent No.: US 12,678,571 B2
(45) Date of Patent: Jul. 14, 2026

(54) VEIN VISUALISATION AID DEVICE

(71) Applicant: MCAS DESIGN LIMITED, Ballincollig (IE)

(72) Inventors: Marie Casey, Ballincollig (IE); Juan F. Martinez, Cork (IE); Andrew De Juan, Cork (IE); Robert Buggy, Cork (IE); Manuel Caballero, Cork (IE)

(73) Assignee: MCAS DESIGN LIMITED, Ballincollig (IE)

( * ) Notice: Subject to any disclaimer, the term of this patent is extended or adjusted under 35 U.S.C. 154(b) by 425 days.

(21) Appl. No.: 18/286,864

(22) PCT Filed: Apr. 21, 2022

(86) PCT No.: PCT/EP2022/060524
§ 371 (c)(1),
(2) Date: Oct. 13, 2023

(87) PCT Pub. No.: WO2022/223677
PCT Pub. Date: Oct. 27, 2022

(65) Prior Publication Data
US 2024/0382696 A1 Nov. 21, 2024

(30) Foreign Application Priority Data

Apr. 23, 2021 (EP) ..................................... 21170317
Jan. 24, 2022 (EP) ..................................... 22153047

(51) Int. Cl.
*A61M 5/42* (2006.01)
*A61B 5/00* (2006.01)
(52) U.S. Cl.
CPC ............. *A61M 5/427* (2013.01); *A61B 5/489* (2013.01); *A61M 5/422* (2013.01);
(Continued)

(58) Field of Classification Search
CPC ....... A61M 5/427; A61B 5/489; A61B 5/0059
See application file for complete search history.

(56) References Cited

U.S. PATENT DOCUMENTS 4,305,401 A 12/1981 Reissmueller et al.
2011/0009751 A1 1/2011 McGuire, Jr. et al.
(Continued)

FOREIGN PATENT DOCUMENTS

DE 10 2011 117470 A1 5/2013
WO 2006/049194 A1 5/2006
(Continued)

OTHER PUBLICATIONS

International Search Report issued in PCT/EP2024/073619; mailed Oct. 10, 2024.
(Continued)

*Primary Examiner* — Andrew H Nguyen
(74) *Attorney, Agent, or Firm* — Studebaker Bracket PLLC

(57) ABSTRACT

A visualisation aid device has a flexible PCB with a ring of surface mount LEDs around a circular opening. The LEDs emit at a wavelength to provide vein visualisation through a skin area exposed by the opening in use. A transparent membrane extends across the needle-access opening, and it has an adhesive on its skin-facing distal side. After insertion of the needle with the benefit of visualisation by the LEDs the substrate may be removed leaving only the membrane maintaining a sterile environment around the puncture site and helping to retain the needle in place.

16 Claims, 9 Drawing Sheets

Figures 1, 2:
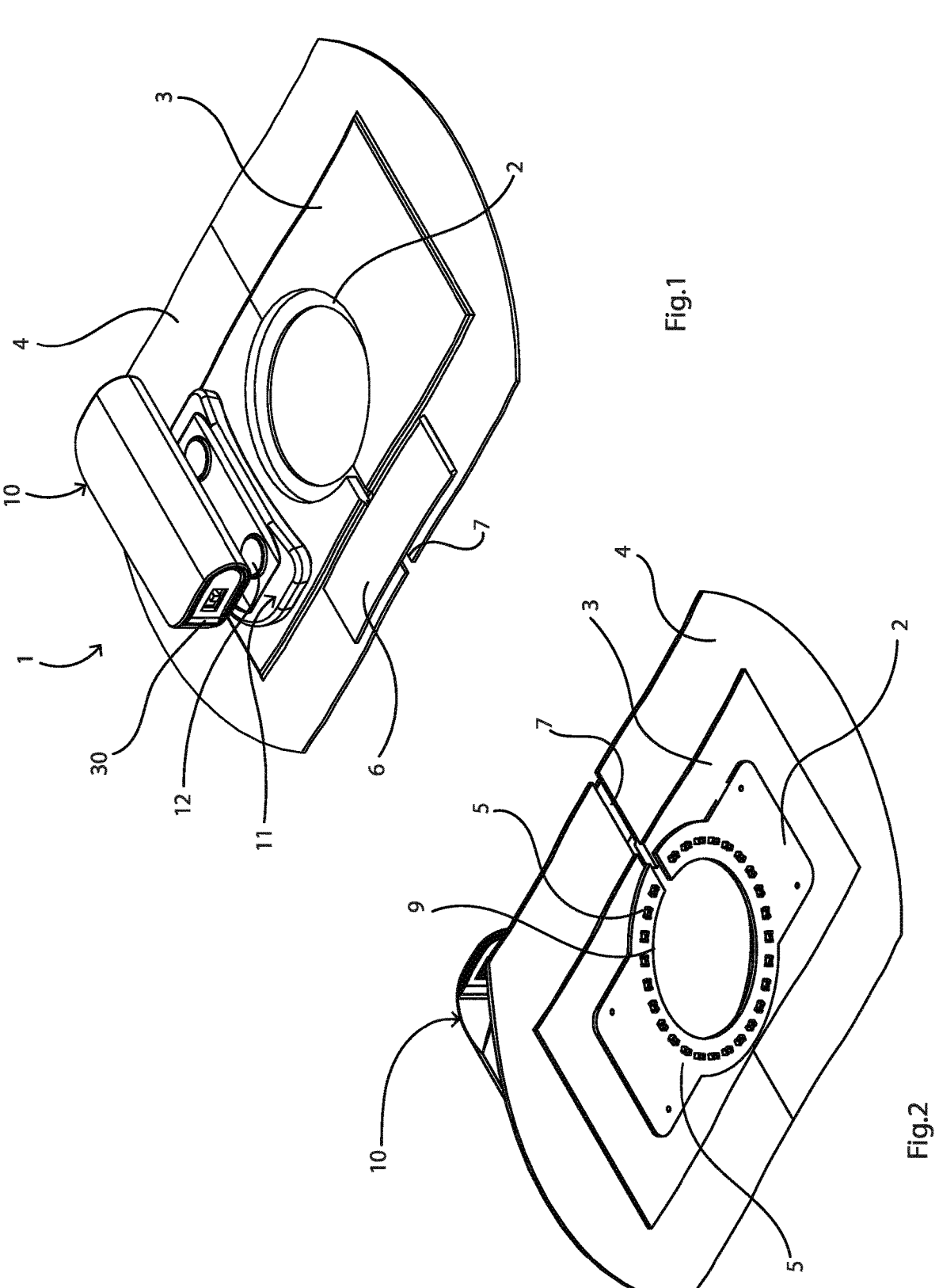

(52) U.S. Cl.
CPC .............. *A61M 2205/0216* (2013.01); *A61M 2205/3306* (2013.01); *A61M 2205/8206* (2013.01); *A61M 2209/06* (2013.01)

(56) References Cited

U.S. PATENT DOCUMENTS

| | | | | |
|---|---|---|---|---|
| 2016/0190741 A1 | 6/2016 | Bulmer et al. | | |
| 2016/0242649 A1* | 8/2016 | Mullani | ................. | A61B 5/489 |
| 2016/0287814 A1* | 10/2016 | McManus | .............. | A61B 90/30 |
| 2019/0387975 A1 | 12/2019 | Goldman et al. | | |
| 2020/0324061 A1* | 10/2020 | Ament | .................. | A61M 5/425 |
| 2023/0191042 A1* | 6/2023 | Yamamoto | ............ | A61M 5/427 |

FOREIGN PATENT DOCUMENTS

| | | | | | |
|---|---|---|---|---|---|
| WO | WO-2007106068 A2 * | 9/2007 | ........... | A61F 13/023 |
| WO | WO-2014035588 A1 * | 3/2014 | .............. | A61M 5/14 |

OTHER PUBLICATIONS

International Search Report issued in PCT/EP2022/060524; mailed Aug. 3, 2022.

\* cited by examiner

If max= 20 mA    Iout = 2 x 180 mA = 360 mA

Vf = 2.2 – 2.8 V    Vdrop = 2 x Vf = 4.4 – 5.6 V

VEIN VISUALISATION AID DEVICE

The substrate forms an annular ring around the opening 9, and there is a radially extending gap 7 which is partially covered over and kept closed by a tear-off strip 6 on the proximal side. This is to hold the device in its original shape until it needs to be removed from a patient's skin, as described in more detail below.

INTRODUCTION

The invention relates to a peripheral venous access aid in humans or animals, for therapeutic treatment, diagnostic, or cosmetic purposes.

It is estimated that over one billion people annually receive a blood test for diagnosis or treatment and/or have an IV inserted. However, a significant number of patients suffer from difficult vein access (DVA). This often leads to significant waste of clinician time and of course discomfort for the patient. Blood draws are often a painful, fearful procedure, and can cause nerve damage and bruising to the patient and needle stick injuries to medical staff.

IV insertion plays a very important role in all types of treatments especially patients with ongoing treatment. Over time blood vessels weaken and this can pose a challenge to health care staff when dealing with elderly patients, and this cohort of patients may not be able to travel easily to their local healthcare practice as a result regular blood tests or treatment may pose a challenge when a vein cannot be located and unnecessary bruising and damage to the vessels can occur.

Patients who need immediate treatment pose another challenge as it may be in a remote area or in an emergency. Vein detection devices are not the best option as the emergency crew can only carry a certain amount of equipment in their emergency kit due to its size and sterilisation options.

It is known to provide aids or devices for improved visualisation. For example, US2016/0242649 (Translite LLC) describes a device for illumination of the skin for enhanced visualization of veins with a switch to select a desired wavelength according to the patient skin colour. US2016/0287814 (Jennus Innovation Corp) describes an illumination device which adheres to the skin to define an illumination window. US2019/0387975 (AccuVein Inc) describes a projection head for improved visualisation.

The present invention is directed towards providing a visualisation aid which is more convenient, simple, and cost effective than current vein detection devices. Another objective is to avoid need for a second person to assist.

SUMMARY OF THE INVENTION

We describe a visualisation device for vein access, the device comprising a plurality of light sources arranged in a pattern on a flexible substrate near an edge of the substrate, and a driver for the light sources, wherein the substrate has an opening for needle insertion, the opening forms a region in the field of emission of the light sources, and there is a gap in the substrate so that the substrate may be peeled away with the needle in place.

Preferably, the substrate forms a generally annular shape around the aperture and said gap extends radially. Preferably, the device further comprises a transparent membrane extending across the opening and said membrane is configured to be punctured by a needle. Preferably, the membrane has adhesive on a distal skin-facing surface, the adhesive allowing the membrane (210) to adhere to the skin surrounding the needle in use to provide a hygienic environment around a puncture site.

Preferably, the substrate is peelable from the membrane after the membrane has adhered to a patient's skin. Preferably, the membrane is of elastomeric material.

Preferably, the substrate comprises a flexible PCB. Preferably, the opening is substantially circular. Preferably, the light sources are LEDs (5), preferably surface mounted.

In one example, the substrate is mounted on a distal side of a resilient pad. Preferably, the device comprises a layer which has an exposed adhesive for adhering to a patient's skin to retain the substrate in place. Preferably, the adhesive layer extends around the substrate on all sides.

Preferably, the substrate is mounted to the distal side of a resilient pad, and the adhesive layer is secured to the proximal side of the pad and extends laterally from said pad.

Preferably, the device comprises a tear-away bridge (6) for retaining opposed sides of the substrate in close proximity at the gap until the tear-away bridge is removed.

Preferably, the driver is removable. Preferably, the device comprises an interface for removable engagement with the driver.

Preferably, the interface and the driver are arranged for physical and electrical engagement to provide drive signals to the substrate. Preferably, the interface and the driver comprise magnets for physical and/or electrical engagement to provide drive signals to the substrate.

Preferably, the interface includes an electrical lead for separate engagement with the driver. Preferably, the device comprises a resilient pad to which the substrate is secured on a distal side, and the interface is secured to the pad on a proximal side. Preferably, the light sources include LEDs which emit at a wavelength in the range of 620 nm to 670 nm.

In some examples, the device comprises a numbing agent adapted to be released to provide a numbing sensation locally to the patient. The numbing agent may comprise a gel capsule, and the agent comprises in one example Lidocaine.

In some examples, the device further comprises a spacer on a distal side of the substrate to provide a separation of at least some light sources from skin, and the spacer may be of a transparent material, and may be around the light sources.

Is some examples, the device further comprises a transparent barrier over at least some light sources on a distal side of said light sources, suitable to reduce heat conduction to the skin in use.

Preferably, the device further comprises a first package which seals the device substrate in a sterile manner, the first package comprising a film which is transparent to the light source emitted radiation, whereby an initial scan of a region on the body may be performed before removal of the device substrate from the package.

Preferably, the device further comprises an external package containing the first package and the device substrate within the first package, the external package having indicia printed for user reading.

We also describe a method of inserting a needle through skin of a human or animal body for treatment, diagnostic, or cosmetic purposes, the method comprising the steps of placing a device of any example on the skin with the light sources facing distally and illuminating a region within said opening, inserting the needle through the skin within said opening with the aid of visualisation provided by the light sources, and removing the substrate with the substrate gap being around the needle.

The method may be performed with a device having a membrane as described herein and the method comprises removing the device substrate after needle insertion and leaving the membrane in place surrounding the skin puncture to provide a sealed sterile environment at the puncture site.

The method may be performed with a device having a first package as described herein and including a step of initially scanning the skin by activation of the light sources and emission of light through the transparent film of the package while the package remains sealed, and continuing use of the device at a region identified in said scan after removal of the device substrate from the package.

We also describe a visualisation device for vein access, the device comprising a plurality of light sources arranged in a pattern on a substrate near an edge of the substrate, and a driver for the light sources.

Preferably, the substrate is flexible. Preferably, the substrate comprises a flexible PCB. Preferably, the substrate comprises an opening and at least some of the light sources are arranged adjacent an edge of said opening.

Preferably, the opening is substantially circular. Preferably, the light sources are LEDs, preferably surface mounted. Preferably, the substrate is mounted on a distal side of a resilient pad.

Preferably, the device comprises a layer which has an exposed adhesive, and which extends laterally from the substrate for adhering to a patient's skin to retain the substrate in place. Preferably, the adhesive layer extends around the substrate on all sides. In some examples, the substrate is mounted to the distal side of a resilient pad, and the adhesive layer is secured to the proximal side of the pad and extends laterally from said pad.

In some examples, the substrate forms an aperture for venous access, and the substrate has a gap connecting with the aperture for peeling the substrate away after use around any needles left in situ. Preferably, the device comprises a tear-away bridge for retaining opposed sides of the substrate in close proximity at the gap until the bridge is removed.

Preferably, the substrate forms a generally annular shape around the aperture, and said gap extends radially from the aperture.

Preferably, the driver is removable. Preferably, the device comprises an interface for removable engagement with the driver. In some examples, the interface and the driver are arranged for physical and electrical engagement to provide drive signals to the substrate. Preferably, the interface and the driver comprise magnets for physical and/or electrical engagement to provide drive signals to the substrate.

In some examples, the interface includes an electrical lead for separate engagement with the driver.

Preferably, the device comprises a resilient pad to which the substrate is secured on a distal side, and the interface is secured to the pad on a proximal side.

Preferably, the light sources include LEDs which emit at a wavelength in the range of 620 nm to 670 nm.

In some examples, the device comprises a numbing agent adapted to be released to provide a numbing sensation locally to the patient. Preferably, the numbing agent comprises a gel capsule, and the agent comprises in one example Lidocaine.

In one example, the substrate forms an enclosure for needle insertion, and which is in the field of view of the light sources, and there is a break in the enclosure so that the substrate may be peeled away with the needle in place, and wherein the device further comprises a transparent membrane extending across the enclosure. The membrane is punctured as a needle is inserted through the enclosure. The membrane has adhesive to adhere to the skin surrounding the needle to provide a hygienic environment around a puncture site, whereby the membrane seals the needle at the injection site in order to avoid infection from occurring.

Preferably, the substrate is peelable from the membrane after the membrane has adhered to a patient's skin. Preferably, the membrane is of elastomeric material.

In one example, the device further comprises a spacer on a distal side of the substrate to provide a separation of at least some light sources from skin, and the spacer may be of a transparent material, and may be around the light sources.

The device may further comprise a covering over at least some light sources, suitable to reduce heat conduction to the skin in use, and such a barrier is preferably transparent.

DETAILED DESCRIPTION OF THE INVENTION

Figure 3:
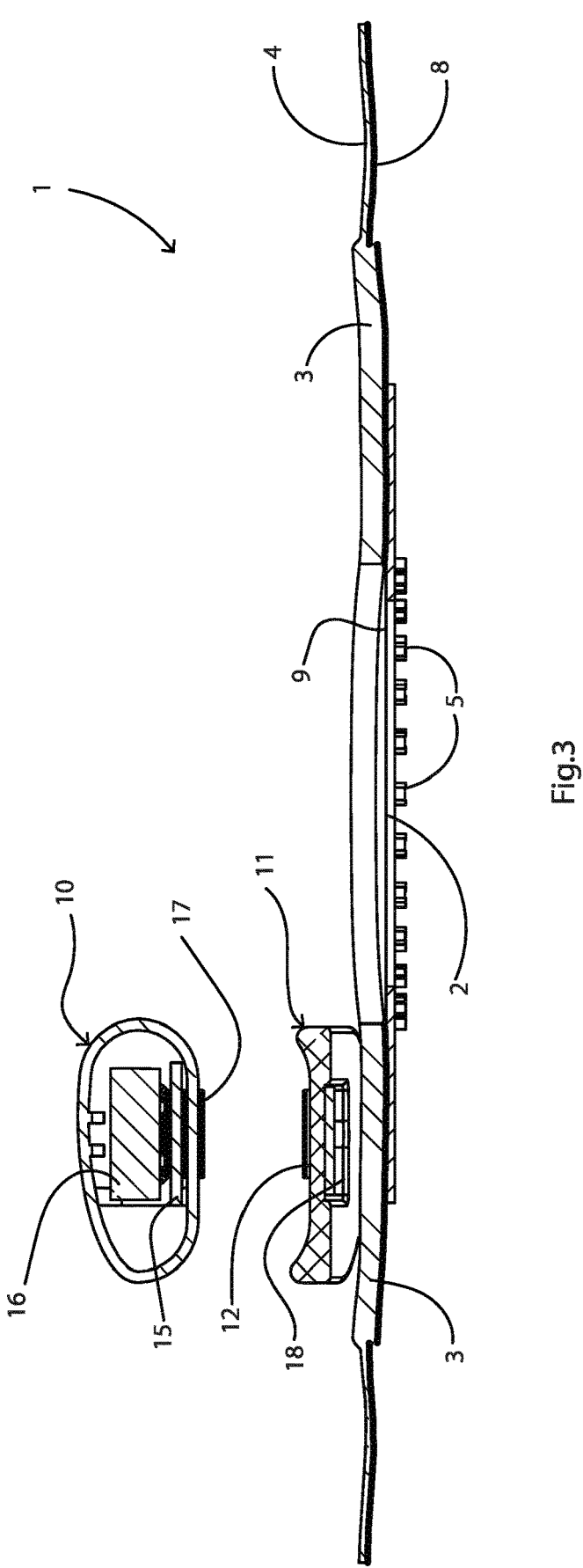
Figure 4:
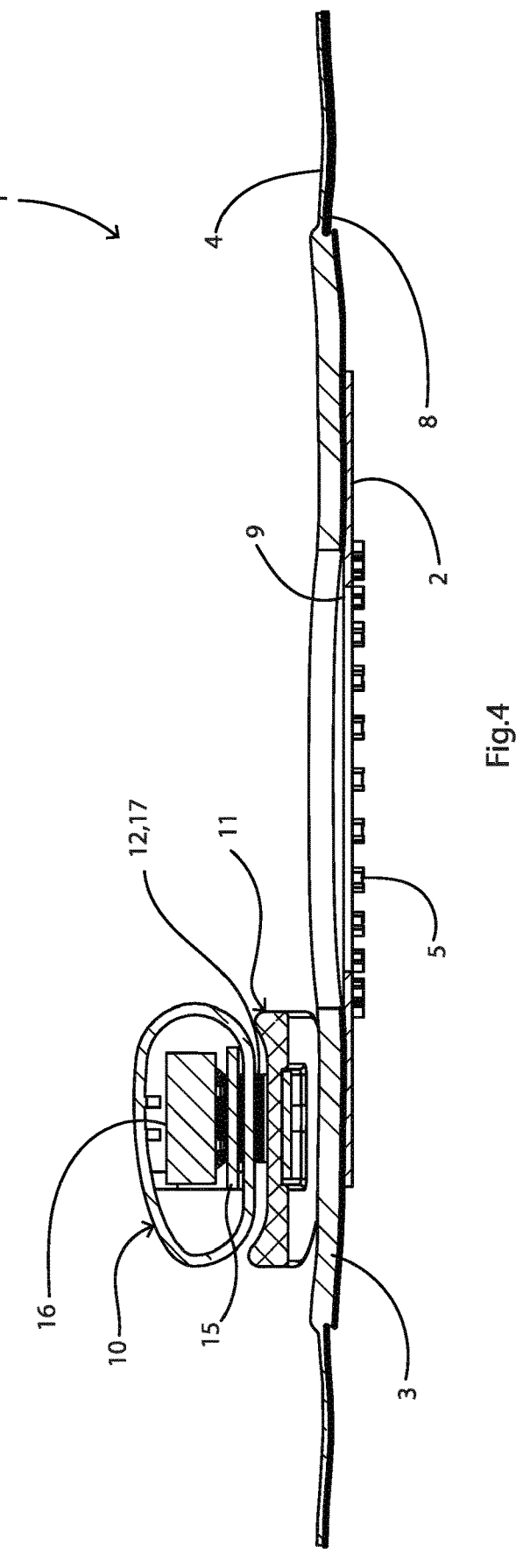
Figure 5:
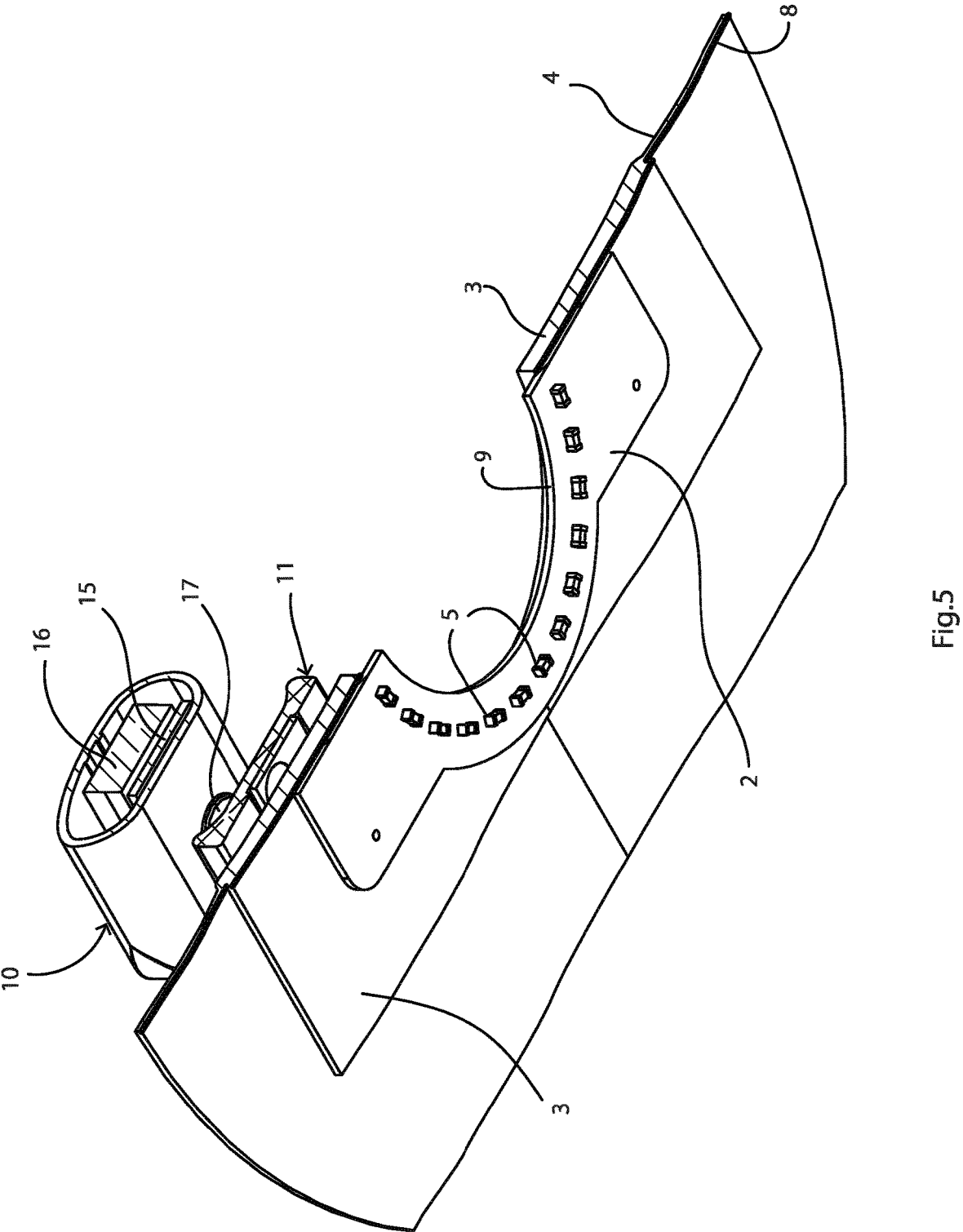
Figure 6:
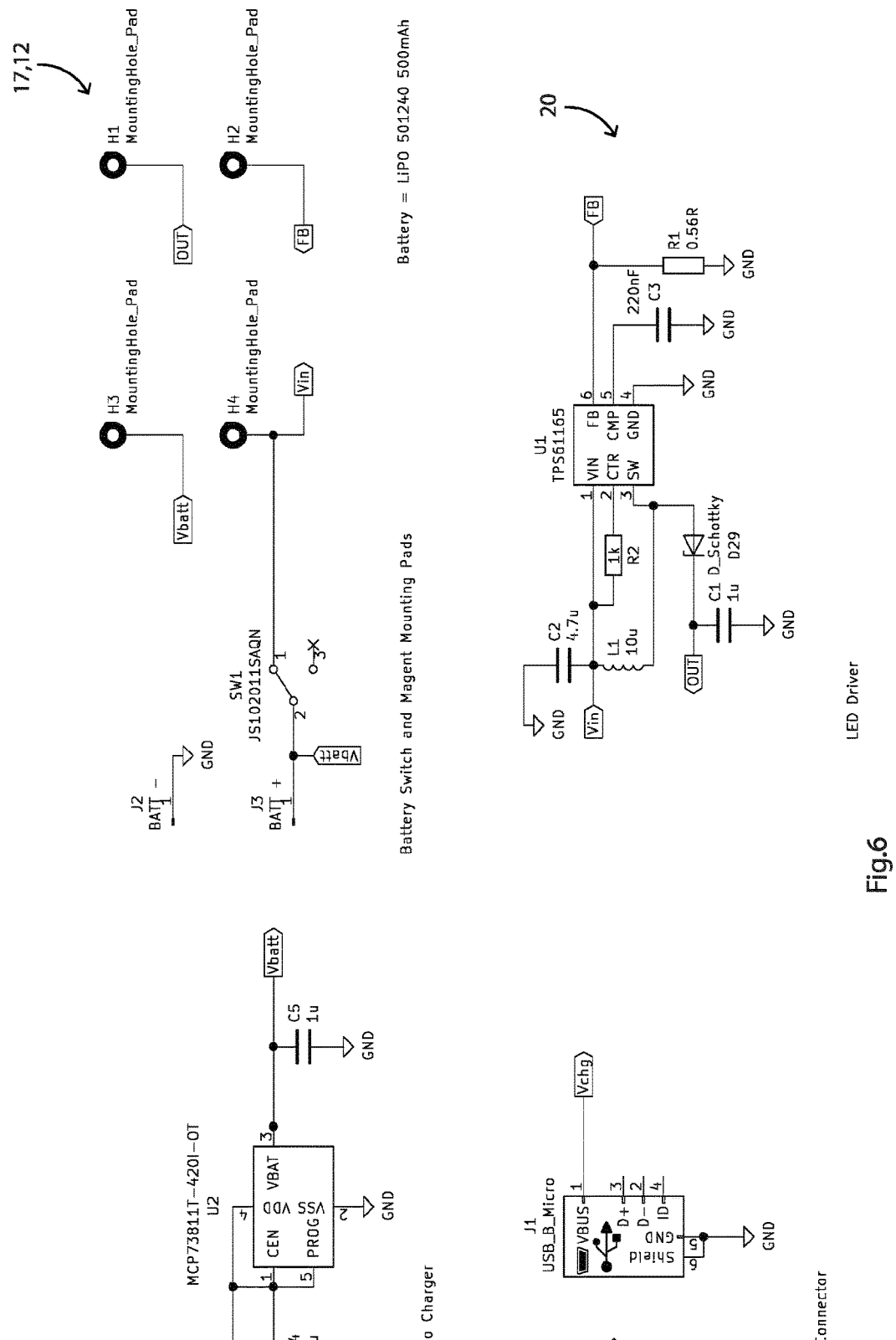
Figure 7:
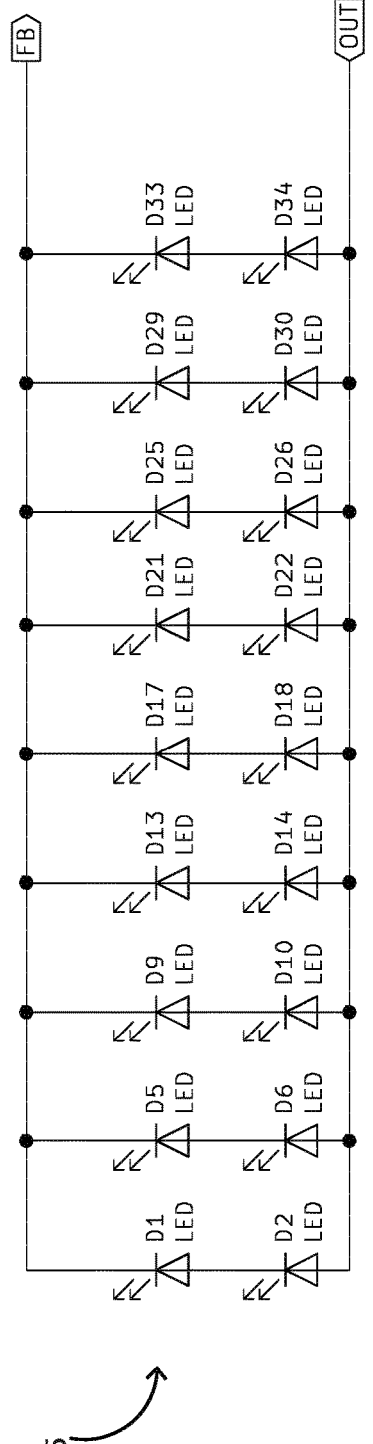
Figure 7:
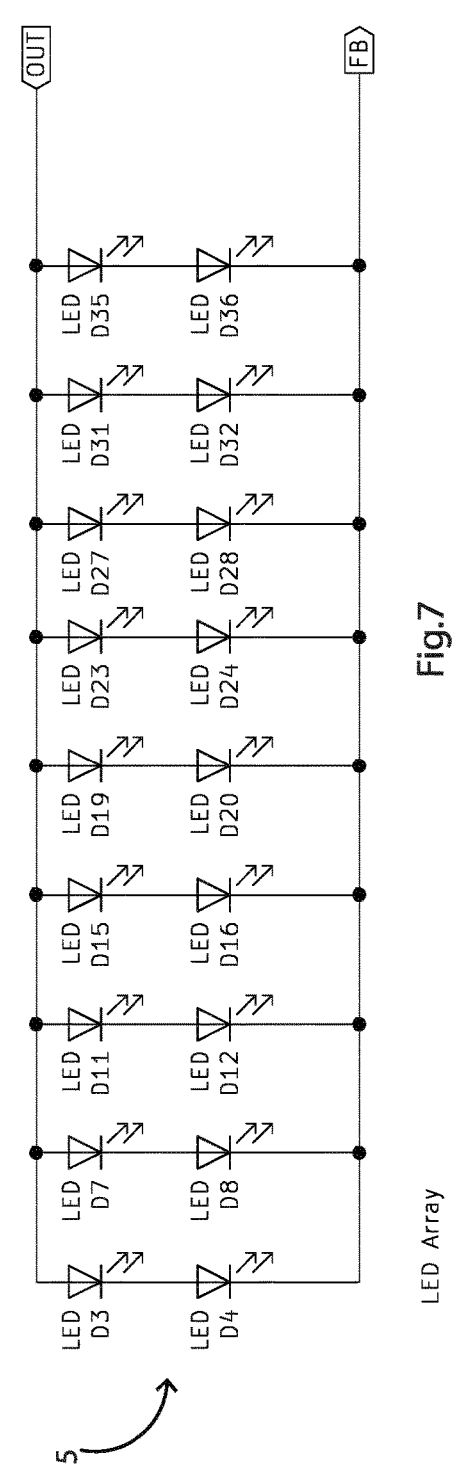
Figure 8:
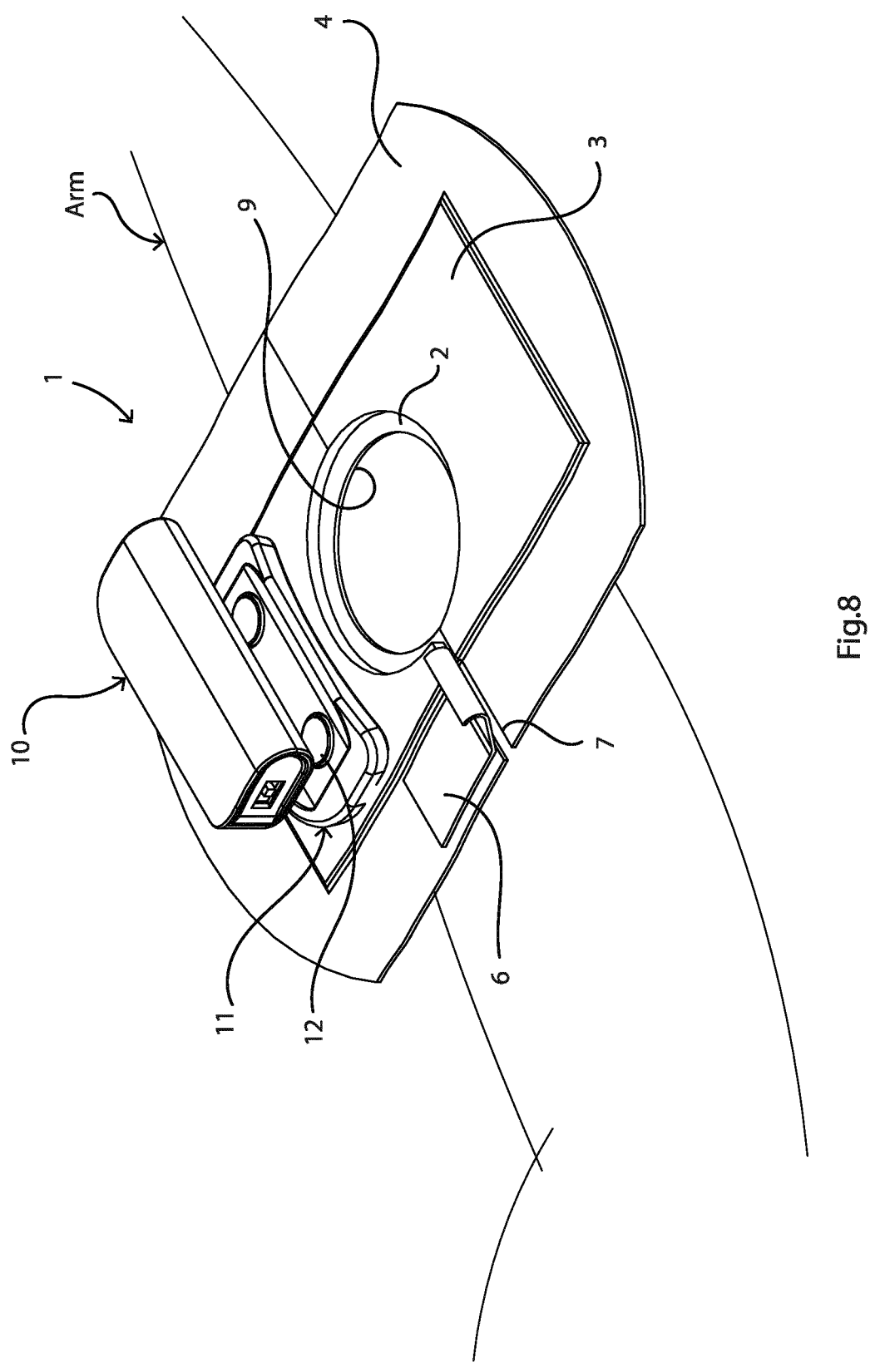
Figures 9, 10:
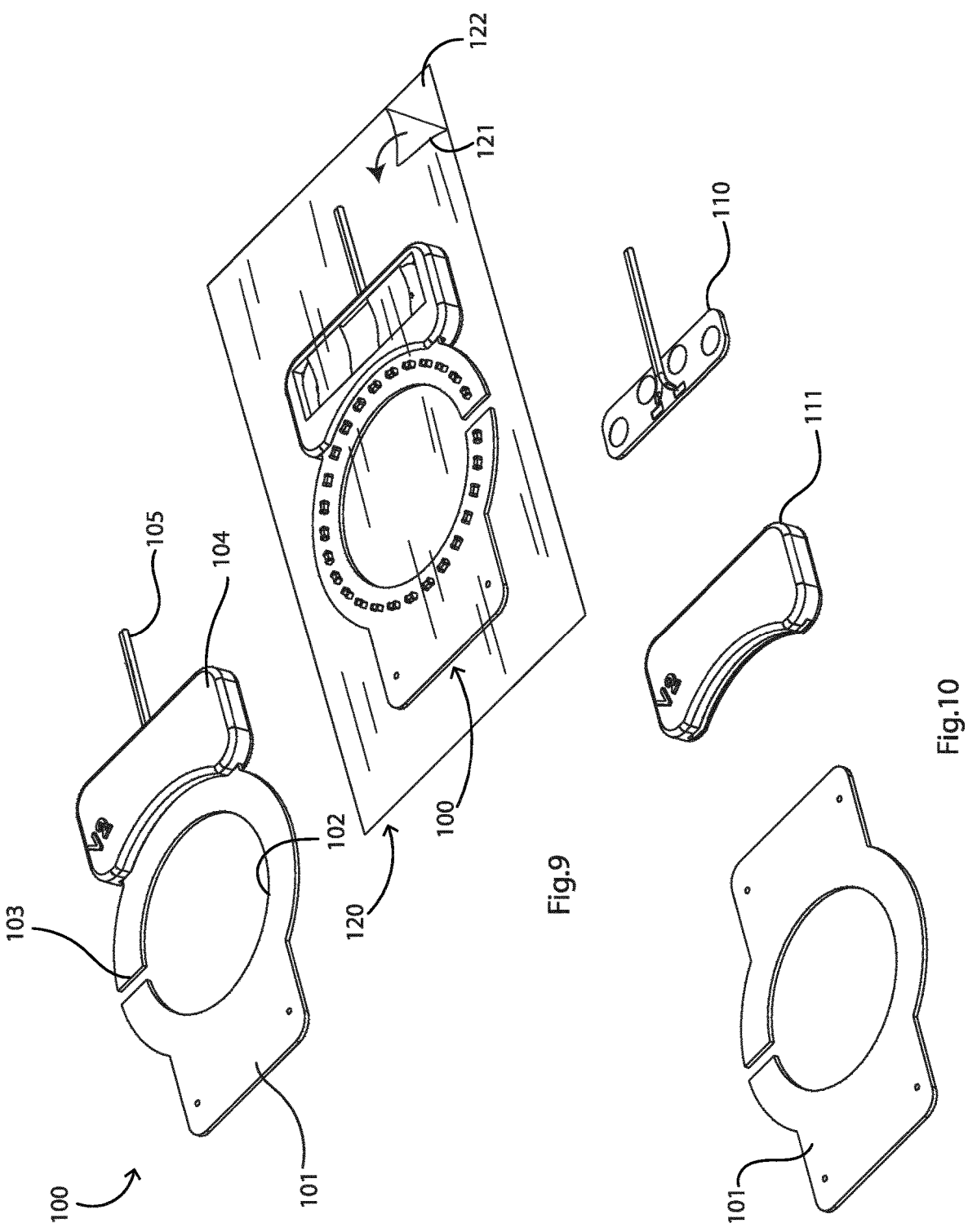

The invention will be more clearly understood from the following description of some embodiments thereof, given by way of example only with reference to the accompanying drawings in which:

FIGS. 1 and 2 are top and underneath perspective views of a vein visualization device of the invention, FIGS. 3 and 4 are cross-sectional views of the device before and after application of a battery pack, FIG. 5 is a cut-away perspective view showing the device in more detail, FIGS. 6 and 7 are circuit diagrams showing the electrical components of the device, FIG. 8 is a perspective view showing the device in use, FIGS. 9 and 10 are perspective views of an alternative device, in which case having an electrical lead for connection with a separate drive located a short distance away, and FIGS. 11(a) to (d) are diagrams illustrating an alternative device with features to both enhance vein visualisation and to maintain a sterile environment around a puncture.

Referring to FIGS. 1 to 4 a vein visualization device 1 comprises a flexible substrate in this case a PCB 2 mounted to a pad 3 on a distal side of the pad, the distal side facing the patient in use. The PCB 2 has a thickness of only 0.7 mm and it supports an array of surface mount LEDs 5 mounted in a ring around a circular opening 9 in the pad 3.

The pad 3 also supports a thin adhesive plaster layer 4 adhered to the pad 3 on the proximal side and surrounding the pad 3 for contact of an adhesive layer 8 on the distal side of the layer 4 to a patient's skin. The materials of the pad and the plaster layer are conventional for any bandage/plaster dressing. The size of the opening 9 in the pad is of 35.0 mm diameter, sufficient to allow adequate space for insertion of a needle in a patient's skin exposed by the opening 9. This adhesive is in one example an acrylic adhesive of the type used in 3M hypoallergenic medical tape. Other suitable adhesives include those used for self-adhesive electrodes as described in https://doi.org/10.1038/s1467-020-18503-8, *"Fully organic compliant dry electrodes self-adhesive to skin for long-term motion-robust epidermal biopotential monitoring"* Lei Zhang et al.

The substrate forms an annular ring around the opening 9, and there is a radially0entending gap 7 which is partially covered over and kept closed by a tear-off strip 6 on the proximal side. This is to hold the device in its original shape until it needs to be removed from a patient's skin, as described in more detail below.

There is a driver interface 11 with a housing supporting a pair of exposed magnets 12, on the proximal side of the pad 3. A removable driver 10 is configured to physically attach to the interface 11 by way of the magnets 17 on the driver 10 engaging magnets 12 of the interface 11. The driver 10 has a PCB 15 with a drive circuit and a battery 16 within a housing. The interface 11 has a PCB 18 linked with the LEDs 5.

There is also a peel-off layer under the plaster 4 and the pad 3, and this isn't shown, for clarity. It is of conventional type as is well known for "plaster" bandages.

Referring particularly to FIGS. 6 and 7, the circuit formed by the driver circuit 15, the interface circuit 18, and the LEDs 5 is shown. This circuit comprises, when the removable driver 10 is engaged, a drive circuit 20, a LiPo charger 21, and a USB connector 22 in the driver 10, the magnets 17 and 12 for transfer of drive signals, and connectors of the interface PCB 18 leading to the LEDs 5. There are 36 LEDs 5, in two separate circuits as shown in FIG. 7.

In use, the device 1 is removed from its sterile packaging (which does not include the removable driver 10), and the peel-off proximal layer (not shown) is removed. The device is applied to the patient's skin as shown in FIG. 8 so that the adhesive 8 adheres to the skin. This leaves an area of the skin exposed by the opening 9. The driver is engaged by simply bringing it into contact with the interface 11, thereby providing both physical and electrical engagement. An ON/OFF switch 30 is closed so that power flows from the battery 16 to the drive circuit 20, and the LEDs 5 are driven.

The LEDs 5 have a pattern, number, intensity, and wavelength for effective illumination beneath the patient's skin. The wavelength provides an orange/red colour of wavelength 620 to 670 nm.

This makes it easy to visualise the veins, and the clinician inserts the needle accurately. This may, for example, involve leaving the needle in place if it is of a catheter. In this case the strip 6 is peeled away, allowing the device to be removed around the needle due to the gap 7.

The two-part assembly allows for attaching the slim profile of the PCB, without the expense of the battery and drive components in the disposable part. The arrangement of the LEDs 5 around the opening 9 provides an optimal ratio of the power requirement and the driver to ensure excellent brightness whilst minimising heat generation. Because the driver 10 is reusable it is possible to have this as a high energy dense lithium-ion battery with a USB port for multiple use.

The snap-fitting of the driver 10 to the interface or cradle 11 with the use of magnets is particularly convenient. It is envisaged that in other embodiments there is no need for a physical ON/OFF switch as switching can be performed automatically upon the magnetic connection being made. Illumination using wavelengths of 620 to 670 nm reaches further horizontal areas, facilitating the user to follow the veins' direction.

It will be appreciated that the removable driver may be linked with the LEDs by way of a wired lead and a separate cradle or plug/socket arrangement. For example, referring to FIGS. 9 and 10 a device 100 has a flexible substrate 101 forming an annular shape around a circular internal aperture 102, around which there are LEDs in an arrangement similar to that of the device 1. Also, there is a gap 103 performing the same function as the gap 7 of the device 1, allowing easier removal if a needle is left in situ. An interface 104 does not in this example directly connect to a driver, but rather an electrical lead 105 extends from it to engage with a separate driver in a plug-in fashion. As shown in FIG. 10 the interface 104 has a low-profile housing 111 and a circuit 110 which is connected to the lead 105. These are shown separately from the substrate 101 for clarity, they are in fact permanently connected and disposable together. The lead 105 may be of any desired length to provide an electrical connection to a separate power source, the physical separation providing for more convenient maintenance of sterility/hygiene of the power source.

This embodiment also allows easy connection to a separate driver which provides the LED drive signals. This embodiment may be modified by inclusion of an adhesive layer around the substrate 101, and there may be a mounting pad, both akin to that of the device 1.

Additionally, the device 100 is provided in a transparent package 120 comprising opposed transparent plastics sheets 121 and 122 which are sealed around their edges to form an enclosure within which the device 100 is sealed in a sterile manner. The package 120 allows the LEDs to be activated for an initial viewing of the veins before the device 100 is removed from its sterile package 120, the films 121 and 122 being transparent. When a desired location is located the package is opened by tearing away one of the films 121/122 as illustrated and the device is then used as described above at the preferred location as determined by the initial trial with the package in place. The package 120 may be an internal package within an external package of conventional construction, with indicia such as product batch identifiers and instructions for use.

It will be appreciated that the embodiments of FIGS. 1 to 10 allow very effective illumination through a patient's skin in an area with a circular border bounded by the LED ring. The substrate takes up a minimal amount of space of skin contact, and it may be easily removed even if there is a needle left in place, due to the gap 7/103. By adhering to the skin, the device can be easily used by a single clinician in an accurate manner. There is excellent sterility because the disposable part can be un-sealed immediately before use.

Embodiment with Elastomeric Needle-Retaining Membrane

Referring to FIGS. 11(*a*) to (*d*) a device 200 has a substrate and LEDs as for the other embodiments: LEDs 202 mounted in a ring on a ring-shaped portion 203 of a substrate 205, and there is a gap 204 in the ring-shaped part 203. These drawings do not show the driver, as this may be in any of the arrangements described above for the other embodiments.

The device 200 in provided in a package akin to the package 120, not shown in these drawings, for clarity. Power may be provided to the LEDs in any of the manners described above, again not shown for clarity.

In the device 200 there is a transparent elastomeric membrane 210 extending across the aperture formed by the substrate ring 203. The membrane 210 is of a material which is approved for such use and in one example is of the type marketed under the trade name Tegaderm™. The membrane 210 is retained to the substrate 203 by its rim being sandwiched between layers of the substrate, with enough retention to keep the membrane in place until it is desired to pull the substrate away. The membrane 210 has adhesive on its distal (skin-facing in use) side. In this example the adhesive is on all of the distal surface of the membrane, however it may alternatively be in a pattern such as concentric rings. As provided in the packaging there is a peel-off cover layer on the adhesive of the membrane 210. The overall device 200 is provided in a sterile individual package (not shown in the drawings), thereby ensuring sterility until the time of use.

In use, the LEDs are activated as described above with reference to FIG. 9 with the package 120 in place, to help locate a good area to insert a needle. The package 120 is then opened so that the device can be used for actual needle insertion.

Figures 11A, 11B, 11C, 11D:
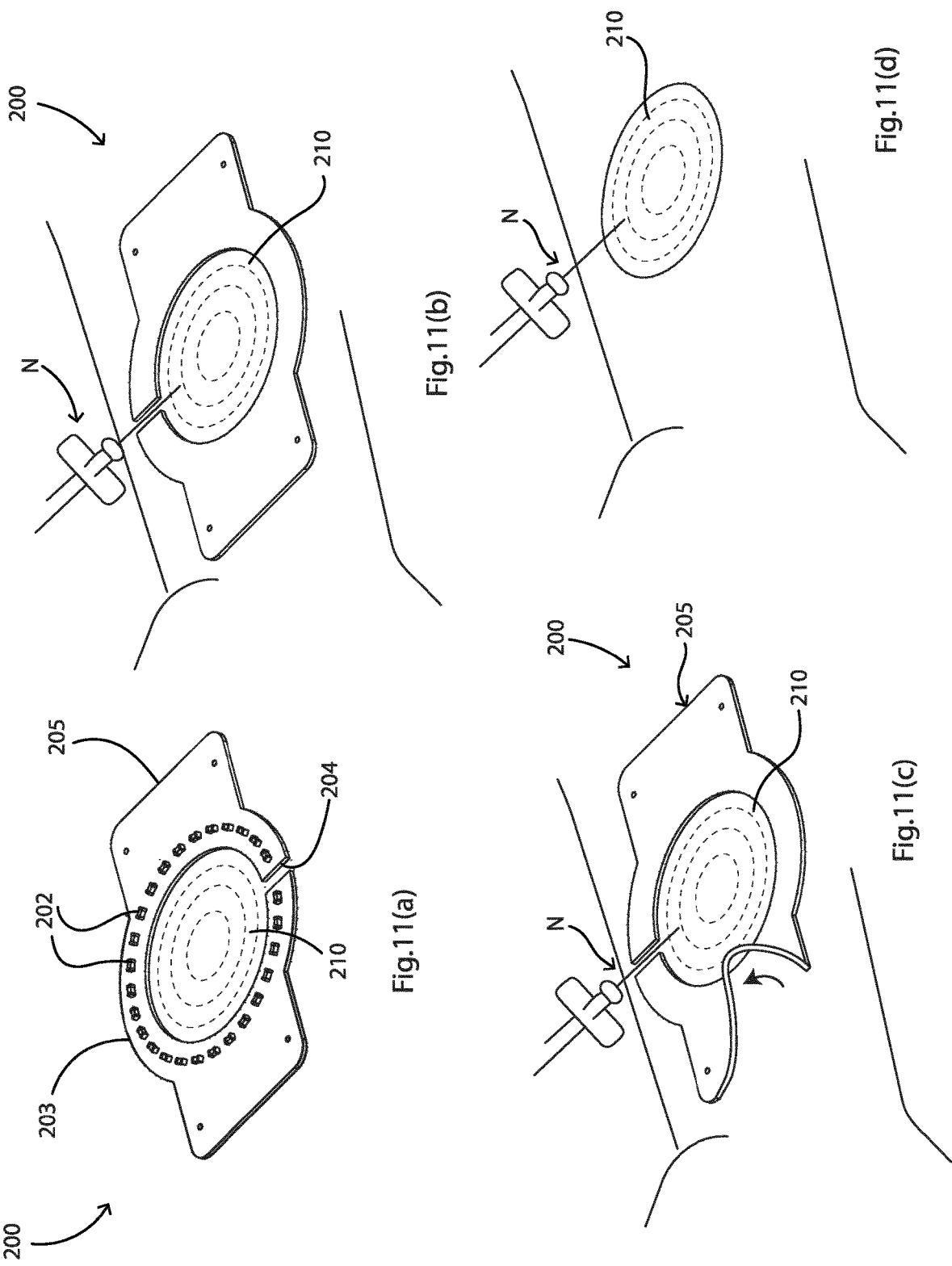

As shown in FIG. 11(b), the device is pressed against the patient's skin so that the LEDs are facing distally, towards the skin and illuminating the region within the ring 203. As described for the other embodiments, this assists with location of a vein for insertion of a needle N. In this case, however, the insertion is through the transparent membrane 210. Hence there is a completely closed environment because the membrane 210 is adhered to the skin. This helps to prevent contamination of the patient in the region where the skin is broken, and also provides protection for the clinician.

As shown in FIG. 11(c), after insertion of the needle N the substrate 201 is peeled away, and the needle is not disturbed, due to the gap 204. The strength of adhesion of the membrane 210 to the skin is greater than the retention strength of the rim of the membrane 210 to the substrate ring 203, and hence the substrate easily separates and peels away.

That leaves, as shown in FIG. 11(d) the membrane 210 in position both helping to keep the needle in place and providing a hygienic environment around the puncture. The clinician is never in direct contact with the patient's skin. Additional dressings may then be applied if required, in conventional manner. There is no need for the clinician to re-palpate the vein to make sure it's the same vein they are targeting It is envisaged that the transparent elastomeric membrane may be retained on the substrate on either the proximal or the distal side of the substrate, and it may extend laterally to engage the skin around the substrate.

By providing a membrane as described the device decreases the number of steps required for intravenous insertion and reduces the number of times required for a clinician to visit the injection site. The device may be conveniently used in any type of medical situation, including emergency use.

In another example the device is provided in a sterile package which is transparent. This allows activation of the LEDs so that the emitted light is transmitted through the transparent packaging and so the device can be used to initially scan the area, before removal of the device from the packaging and full use of the device with attachment to the skin at the identified area.

This transparent package may be an inner package, within an outer conventional package for transport and handling of the device before use, and to provide instructions for use. Enhancement of the Effect of the LED Illumination In some embodiments there is provided (to enhance the LED's effect) a circular transparent silicone ring surrounding the LED's facing distally (onto the skin in use). This may enhance the depth of some light wavelengths, especially amber light. This is to create more depth, enhancing the effect of the LEDs, especially for darker coloured skin.

In another variation a transparent ring of material such as silicone may be mounted over the LEDs. This can both help to enhance the illumination be providing greater depth and it can act as a barrier to protect the skin from over-heating.

In another variation, a magnification lens, which may be in the form of a transparent coating over the LEDs, is mounted to allow more accurate and enhanced vein visualisation.

Advantages

The small form factor with reduced footprint for ease of use and impact on end-of-life of the device are also advantageous, as is the flexibility for adhering to uneven surfaces, particularly on the forearm. Also, by being self-adhering the device eliminates need for a second person to assist, enabling single person operation. It is envisaged that the device can be included in most medical kits where practitioners can quickly make use of the device as a useful aid for emergency cannulation. Although not limited to fast-paced, critical scenarios, the device helps streamline the process by making it usable by a single person.

The device can be used in any situation where one needs to locate a vein for insertion of a needle into the vein, or indeed to avoid the vein and inject into muscle. Regarding the latter avoidance of a vein may be important for diabetics and in the beauty industry for fillers where it's important not to inject into a vein to avoid risk of infection.

A major benefit of the invention is that it addresses the problem of there being a wide range of competency across clinicians in the task of locating a vein, especially for DVA patients.

The user will require minimum training, the main procedure being placing battery on the cradle to activate it, scan the area, press onto the skin, continue procedure, peel off, and dispose of all but the battery.

The device is particularly helpful at preventing need for recurrent attempts to insert a needle to gain access to a vein, thereby avoiding anxiety, pain, and distress and elevated the risk of damaging the veins and causing infiltration of the surrounding area and the subsequent possibility of a catheter-related, hospital acquired bloodstream infection. It is especially advantageous in ad hoc emergency situations where preliminary intravenous procedures can be conducted. Studies shows that excessive venipunctures are both time- and resource-consuming events, which cause anxiety, pain, and distress in patients, or can lead to severe harmful injuries. The device facilitates optimum intravenous procedures The issue of the risk of cross-contamination is also addressed by many of the components being for single-use only. The thin board 2 is fully integrated into the bandage-type pad and plaster.

The invention provides for high intensity with minimum thermal load by utilising high density SMD LEDs technology which are spatially distributed for optimum performance. The invention also provides the benefits of:

very low-profile, flexibility, that adapts and conforms to the shape of the arm and or any other body part for better performance through transillumination, detachable and rechargeable driver with battery, seamless magnetic connection between the driver and the LED illumination ring.

utility, enabling the medical practitioner to operate without the need for an assistant or the patient to hold the device in place with the 'peel and stick' approach, and high-energy dense power source that maintains its small footprint which is an advantage to deal with the younger demographic (i.e. children)

The device is particularly suited to situations such as identification of a vein for a blood draw and IV cannulation insertion.

The device may have in some examples an add-on gel capsule (such as of Lidocaine) to numb the area before procedure commences. The shield is particularly effective because it provides a number of important advantageous functions. It shields the clinician from blood spray, it visually helps to define the venous access space due to the curved shield edge, and it optically aids visualisation due to the shield orange-red colour.

The device can advantageously be used to avoid a vein which is the case in certain cosmetic procedures and patients with certain medical conditions.

The device eliminates the need to sterilise between each patient as each device is pre-sterilised and individually packaged. An envelope over the aid act as a very effective second barrier.

The invention is not limited to the embodiments described but may be varied in construction and detail, for example to suit the size of the individual patient or animal. For example, at least some of the LEDs may be recessed in cavities in the substrate. They may be in any desired arrangement for optimum illumination relative to the intensity of each individual LED, for example in an array of two or more rows. Also, there may be a protective cover or film over the LEDs, which may for example be transparent strip adhered over the LEDs and the downwardly facing housing surface. In some embodiments a protective layer or film will protect the patent's skin from overheating as LED's can feel warm on the skin depending on how long they are left on the skin by the Clinician however due to light intensity it allows the Clinician to locate a vein more quickly.

Also, it is envisaged that there may not be an adhesive layer, merely the flexible LED substrate linked by a cable to the battery cradle. Such an arrangement comprises only the substrate 2 and the LEDs 5 and a wired lead to the separate cradle 11 for connection to removable drive 10.

The invention claimed is:

1. A visualisation device for vein access, the device comprising:
a plurality of surface mounted LED light sources arranged in a pattern on a flexible substrate near an edge of the flexible substrate,
a driver for the light sources,
the flexible substrate including an opening for needle insertion, said opening forming a region in a field of emission of the light sources, and there is a gap in the flexible substrate so that the flexible substrate may be peeled away with a needle in place, and wherein the substrate forms a generally annular shape around the opening and said gap extends radially, and
a transparent membrane extending across the opening of the flexible substrate and said membrane is configured to be punctured by the needle, wherein the membrane has an adhesive layer on a distal skin-facing surface, the adhesive layer allowing the membrane to adhere the membrane to a patient's skin surrounding the needle in use to provide a hygienic environment around a puncture site, and wherein the substrate is peelable from the membrane after the membrane has adhered to the patient's skin, being of elastomeric material,
the driver being removable, in which the device comprises an interface for removable engagement with the driver and the interface and the driver being arranged for physical and electrical engagement to provide drive signals to the substrate, and

the interface includes an electrical lead for separate engagement with the driver.

2. The visualisation device as claimed in claim 1, wherein the substrate comprises a flexible PCB.

3. The visualisation device as claimed in claim 1, wherein the substrate is mounted on a distal side of a resilient pad.

4. The visualisation device as claimed in claim 1, wherein the device comprises an exposed portion of the adhesive layer for adhering to the patient's skin to retain the substrate in place.

5. The visualisation device as claimed in claim 4, wherein the adhesive layer extends around the substrate on all sides.

6. The visualisation device as claimed in claim 5, wherein the substrate is mounted to a distal side of a resilient pad, and the adhesive layer is secured to a proximal side of the pad and extends laterally from said pad.

7. The visualisation device as claimed in claim 1, wherein the device comprises a tear-away bridge for retaining opposed sides of the substrate in close proximity at the gap until the tear-away bridge is removed.

8. The visualisation device as claimed in claim 1, wherein the device comprises a resilient pad to which the flexible substrate is secured on a distal side of the pad, and the interface is secured to the pad on a proximal side of the pad.

9. The visualisation device as claimed in claim 1, wherein the light sources include LEDs which emit at a wavelength in the range of 620 nm to 670 nm.

10. The visualisation device as claimed in claim 1, wherein the device comprises a numbing agent adapted to be released to provide a numbing sensation locally to the patient.

11. The visualisation device as claimed in claim 10, wherein the numbing agent comprises a gel capsule, and the agent comprises Lidocaine.

12. The visualisation device as claimed in claim 1, further comprising a spacer on a distal side of the flexible substrate to provide a separation of at least some of the light sources from the skin.

13. The visualisation device of claim 1, further comprising a spacer on a distal side of the flexible substrate to provide a separation of at least some of the light sources from the skin, and the spacer is of a transparent material.

14. The visualisation device as claimed in claim 1, further comprising a transparent barrier over at least some of the light sources on a distal side of said light sources, suitable to reduce heat conduction to the skin in use.

15. The visualisation device as claimed in claim 1, further comprising a first package which seals the flexible substrate in a sterile manner, the package comprising a film which is transparent to light source emitted radiation, whereby an initial scan of a region on a body may be performed before removal of the flexible substrate from the package.

16. The visualisation device as claimed in claim 15, further comprising an external package containing the first package, the external package having indicia printed for user reading.

* * * * *